United States Patent
Akerele

(10) Patent No.: US 12,293,816 B2
(45) Date of Patent: May 6, 2025

(54) SYSTEMS, DEVICES, AND METHODS INCLUDING COLOR-CODED SUBSTRATES FOR SPOT-CORRECTION OF BLEMISHES, ACNE, AND SECONDARY SKIN CONCERNS

(71) Applicant: L'Oreal, Paris (FR)

(72) Inventor: Dominic Akerele, Brooklyn, NY (US)

(73) Assignee: L'Oreal, Paris (FR)

( * ) Notice: Subject to any disclaimer, the term of this patent is extended or adjusted under 35 U.S.C. 154(b) by 381 days.

(21) Appl. No.: 17/821,663

(22) Filed: Aug. 23, 2022

(65) Prior Publication Data

US 2023/0065050 A1     Mar. 2, 2023

Related U.S. Application Data

(60) Provisional application No. 63/237,023, filed on Aug. 25, 2021.

(30) Foreign Application Priority Data

Dec. 1, 2021 (FR) ..................... 2112798

(51) Int. Cl.
    *G06V 10/00*     (2022.01)
    *G06T 7/00*     (2017.01)
    (Continued)

(52) U.S. Cl.
    CPC ........... *G16H 20/10* (2018.01); *G06T 7/0012* (2013.01); *G06T 7/90* (2017.01);
    (Continued)

(58) Field of Classification Search
    CPC ...... G16H 20/10; G16H 30/20; G06T 7/0012; G06T 7/90; G06T 2207/10024; G06T 2207/10048; G06T 2207/30088
    See application file for complete search history.

(56) References Cited

U.S. PATENT DOCUMENTS

2016/0089308 A1    3/2016   Mohammadi et al.
2017/0251130 A1    8/2017   Shinoda
(Continued)

FOREIGN PATENT DOCUMENTS

| EP | 2648569 A1 * | 10/2013 | ........... A45D 44/002 |
|---|---|---|---|
| EP | 2648569 B1 | 9/2018 | |
| WO | 2020183350 A1 | 9/2020 | |

OTHER PUBLICATIONS

Iwang et al., Multifunctional Smart Skin Adhesive Patches for Advanced Health Care, Advanced Healthcare Materials, vol. 7, No. 15, May 14, 2018, 20 pages.
(Continued)

*Primary Examiner* — Vu Le
*Assistant Examiner* — Zaid Muhammad Saleh
(74) *Attorney, Agent, or Firm* — Christensen O'Connor Johnson Kindness PLLC

(57) ABSTRACT

A computer-implemented method and system for tracking skin concerns. Color-coded substrates come in different colors, each color being associate with a different skin concern. The color-coded substrates include at least one hydrocolloid and active agent. The color-coded substrates can come in different area-specific shapes for applying on different areas of the skin or face. The color-coded substrates can come in different dosages. A computing device, such as a smartphone, can be used to take scans of the skin with or without substrates, and the computing device is configured to analyze the skin and color-coded substrates based on color or shape or other symbols to make recommendations so that a subject will be able to track the progress of any skin concern.

23 Claims, 10 Drawing Sheets

(51) Int. Cl.
*G06T 7/90* (2017.01)
*G16H 20/10* (2018.01)

(52) U.S. Cl.
CPC .............. *G06T 2207/10024* (2013.01); *G06T 2207/10048* (2013.01); *G06T 2207/30088* (2013.01)

(56) References Cited

U.S. PATENT DOCUMENTS

| | | |
|---|---|---|
| 2017/0270350 A1 | 9/2017 | Maltz et al. |
| 2019/0111005 A1* | 4/2019 | Frezza .................... A61L 15/46 |
| 2019/0298038 A1 | 10/2019 | Miles |
| 2020/0121565 A1* | 4/2020 | Smith .................... A61Q 19/02 |
| 2020/0170564 A1 | 6/2020 | Jiang et al. |
| 2020/0342213 A1* | 10/2020 | Dissanayake ........ A61B 5/7435 |
| 2020/0411186 A1 | 12/2020 | Blanchard et al. |
| 2023/0063088 A1 | 3/2023 | Akerele |

OTHER PUBLICATIONS

International Search Report and Written Opinion, mailed Dec. 16, 2022, in corresponding International Patent Application No. PCT/US2022/075344, 11 pages.
FR Preliminary Search Report FA902926 FR2112798.

\* cited by examiner

SYSTEMS, DEVICES, AND METHODS INCLUDING COLOR-CODED SUBSTRATES FOR SPOT-CORRECTION OF BLEMISHES, ACNE, AND SECONDARY SKIN CONCERNS

CROSS-REFERENCE(S) TO RELATED APPLICATION(S)

This application claims the benefit of U.S. Provisional Application No. 63/237,023, filed on Aug. 25, 2021; and claims priority to French Patent Application No. 2112798 filed on Dec. 1, 2021; the contents of which are herein expressly incorporated by reference in their entirety for all purposes.

SUMMARY

This disclosure is directed to color-coded substrates (e.g., bandages, patches, carriers, tapes, and the like) that are manually placed by a subject on corresponding affected skin concern areas, such as acne, pigmentation, post inflammatory hyper-pigmentation (PIH), wrinkles, fine lines, or any other skin concern a subject is treating. In an embodiment, the color-coded substrates act as both a treatment for the selected apparent skin concern and a medium for tracking the progress and development of future skin care concerns. In an embodiment, the skin concern tracking is enabled by taking an image through a native mobile and web application that processes the image and tags the affected skin areas based on the concern that corresponds to the color-coded substrate that is present in the affected area. In an embodiment, during use, the user is then able to track changes in their skin concerns visualized through a personalized heat map of the user's skin care concerns that are updated after each full use of the substrates and image capture.

In one example, hydrocolloid substrates with concentrated skin care treatment formulas specific to treating and correcting apparent skin concerns include one or more active agents to treat skin conditions, including, for example, acne, pigmentation, post inflammatory hyper-pigmentation (PIH), wrinkles, and fine lines.

In one example, visual imaging and image processing is facilitated through a mobile phone or web based camera and image processing algorithm to detect the presence of the color-coded substrates and assess the differences of the substrates corresponding to different skin care concerns represented by the unique physical color code.

In one example, the image processing and algorithm development also enable the visualizations of the user's skin care concern tracking over time.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
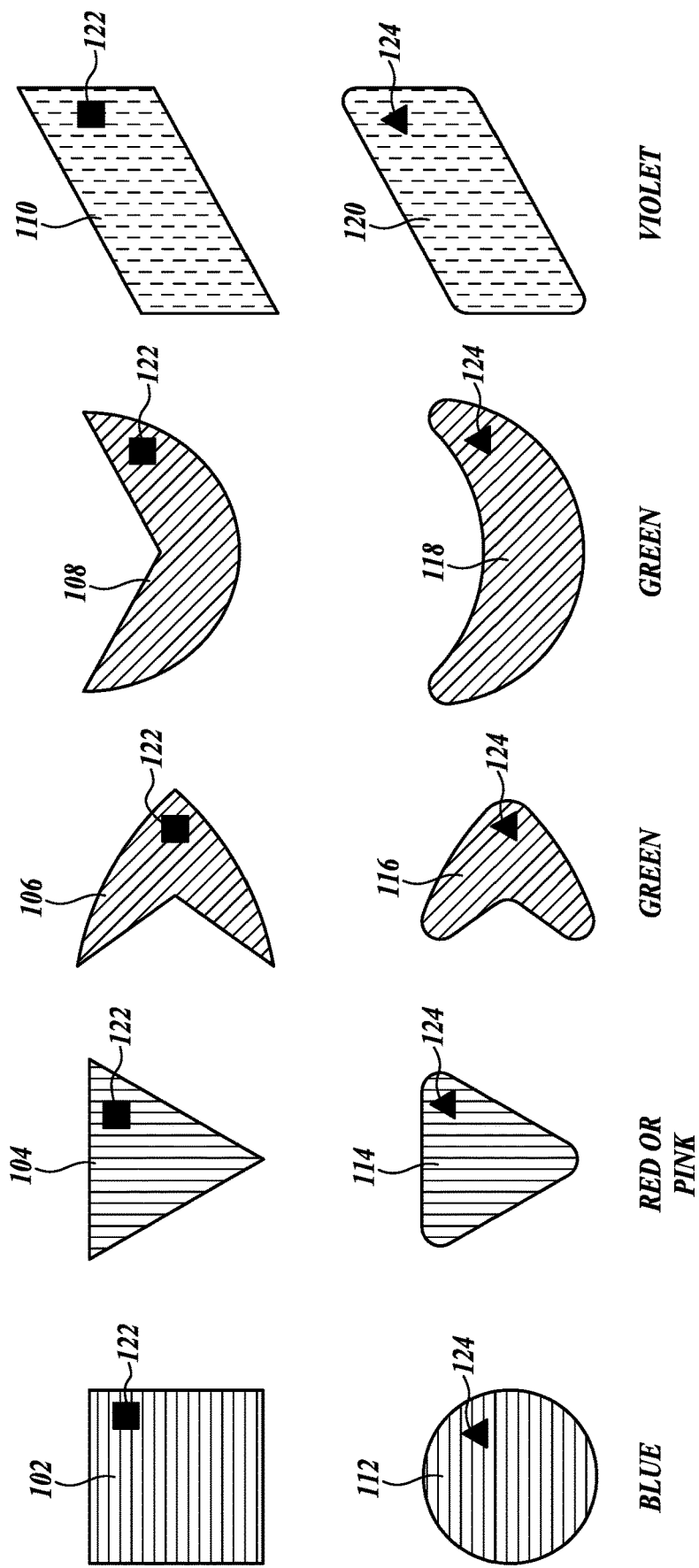
FIG. 1 is a diagrammatical illustration of examples of color-coded substrates having area-specific shapes.

Referring to FIG. 1, embodiments of color-coded area-specific substrates (e.g., color-coded area-specific bandages, color-coded area-specific patches, color-coded area-specific carriers, color-coded area-specific tapes, and the like) 102, 104, 106, 108, 110, 112, 114, 116, 118, and 120 are illustrated. The view in FIG. 1 is from the top side of the substrates. The tops of the substrates will have a visibly perceptible color code applied. In FIG. 1, the color is represented by a particular line hatching according to the United States Patent and Trademark Office manual.

In one embodiment, the horizontal lines of color-coded substrates 102, 112 represent blue. In one embodiment, the vertical lines of color-coded substrates 104, 114 represent red or pink. In one embodiment, the diagonal lines of color-coded substrates 106, 116, 108, 118 represent green. In one embodiment, the dashed vertical lines of color-coded substrates 110, 120 represent violet or purple. However, the color codes used for substrates can be any color and are not limited to the colors represented in FIG. 1. The color of the color-code substrate allows the substrate to be recognized from an image taken from any device with a camera, such as, mobile devices including smartphones, tablets, and the like, including an image processing application and/or a spectrometer.

The bottom side of the color-coded substrates can be configured for application or adhesion onto a skin surface to treat one of several skin concerns. In the examples, the color-coded substrates 102, 104, 106, 108, 110, 112, 114, 116, 118, and 120 can have a different color, wherein a color represents the skin concern intended to be treated, and therefore, different active agents are included in the color-coded substrates of dissimilar color. In one example, color codes may be defined by a wavelength range of a portion of the visible light spectrum that is generally from about 380 nm corresponding to violet to about 700 nm for red.

In the examples, the color-coded substrates 102, 104, 106, 108, 110, 112, 114, 116, 118, and 120 can further have area-specific shapes that are intended to conform to specific areas of the skin or face and can accommodate certain contoured areas of the face. In the examples, the color-coded substrates 102, 104, 106, 108, 110, 112, 114, 116, 118, and 120 can further have area-specific geometries that are intended to conform to specific areas of the skin or face and can accommodate certain contoured areas. For example, the square and circle substrates 102, 112 may be for the forehead and cheeks, the triangle shaped substrates 104, 114 may be for the glabella, the chevron shape substrates 106, 116 may be for the corners of the eyes and mouth, the crescent shape substrates 108, 118 may be for under the eyes, cheekbone, or chin, and the parallelogram shape substrates may be for the cheek or jawline.

In the examples, since color-coded substrates can have active agents that may cause undesirable effects when in close proximity to other active agents, the color-coded substrates can be provided in sets that are compatible with each other. In examples, various compatible sets can be provided, wherein color-coded substrates in the compatible set have active agents that are all compatible with other active agents in the compatible set. One advantage is to give subject choices for active agents. If a subject has an allergy or is sensitive to some active agents, then, a subject can be provided with color-coded substrates to which the subject has no allergic reactions and no sensitivity.

In the top row in FIG. 1, the shapes of the color-coded substrates 102, 104, 106, 108, and 110 have at least one angle formed from two straight lines. In this example, the color-coded substrates 102, 104, 106, 108, and 110 only have active agents that are compatible with each other, and the shape with at least one angle indicates that any color-coded substrate with at least one angle will be compatible with any other color-coded substrate with at least one angle.

In the bottom row in FIG. 1, the shapes of the color-coded substrates 112, 114, 116, 118, and 120 have no angles formed from two straight lines. In this example, the color-coded substrates 112, 114, 116, 118, and 120 have active agents that are compatible with each other, and the shape without any angles indicates that any color-coded substrate with no angle will be compatible with any other color-coded substrate with no angles.

However, it is possible that not all active agents of the set of color-coded substrates 102, 104, 106, 108, 110 are incompatible with all the active agents of the set of color-coded substrates 112, 114, 116, 118, and 120. It is possible that color-coded substrates 102, 104, 106, 108, 110 can be used with the color-coded substrates 112, 114, 116, 118, 120 when there is no incompatibility or when the color-coded substrates are spaced far apart that the active agents do not interfere with each other.

In the examples, the compatibility may also be determined by including a symbol on the color-coded substrates. For example, the color-coded substrates 102, 104, 106, 108, and 110 have a small square 122 to signify compatibility among substrates with small squares. The color-coded substrates 112, 114, 116, 118, and 120 have a small triangle 124 to signify compatibility among substrates with small triangles.

By using either a particular shape feature or a symbol on the color-coded substrates, it can be possible for an image processor to perform analysis of an image and identify the shapes of the color-coded substrates or recognize the symbols to determine compatibility.

While it may be preferable to select the use of color-coded substrates from the set of substrates whose active agents are compatible, in some examples, it is possible to combine color-coded substrates from one compatible set with another color-coded substrate from a different compatible set. For example, the two color-coded substrates whose active agents are not compatible can be used at distances where the active agents would not interfere with each other. An image processor can analyze an image to determine whether a color-coded substrate from one compatible set is a suitable distance from a color-coded substrate from a different compatible set.

The color-coded substrates may come pre-packaged according to active agent compatibility. The color-coded substrates may also come in different dosages of active agents. In an example, a color spanning a waveband determines the skin concern, and the particular shade of color determines the dosage level. A light color may indicate a lower dosage of an active agent, and a dark color in the same waveband may indicate a higher dosage of the same active agent.

In an example, for every skin concern that can be treated, the color-coded substrates may come in different shapes. For example, color-coded substrates for the skin concern "acne" may come in all the area-specific substrates. For example, color-coded substrates for treatment of acne can come in square or circle for the forehead, triangle for the glabella, chevron for the corner eyes or lips, crescent for under the eyes or on the cheekbone, and parallelogram for the cheek or jawline. Therefore, substrates for treating each skin concern come in multiple area-specific shapes, as well as in multiple dosages, and in multiple compatible sets.

In one example, the color blue can designate a substrate to treat dark spots or pigmentation, the color violet or purple can designate a substrate to treat post inflammatory hyperpigmentation, and the color red to treat acne. The color green can treat age lines or wrinkles. There is no limit to the number of different colors that the color-coded substrates can come in and the skin concerns to be treated.

Compositions useful in the treatment of dark spots, acne, pigmentation, post inflammatory hyperpigmentation, age lines, and wrinkles are known and can be incorporated into the substrates 102, 104, 106, 108, 110, 112, 114, 116, 118, and 120.

In an embodiment, the substrates 102, 104, 106, 108, 110, 112, 114, 116, 118, and 120 include a structure including one or more layers that can be applied to and/or removed from the skin. In an embodiment, the color-coded substrates 102, 104, 106, 108, 110, 112, 114, 116, 118, and 120 include a composition including a hydrophilic gelling system that forms a layer capable of being applied to and/or removed from the skin. The composition includes at least one active agent for the particular skin concern, wherein the active agent is configured to interact with the skin, whether by diffusion into the skin (through the dermis) or by surface contact. The active agents in the composition may escape from the substrate during application or adhesion of the substrate to the skin. Depending on the type of interaction between the substrate and the skin, the application time can vary from about a few seconds to about a few hours, or even to about a few days.

In an embodiment, the color-coded substrates 102, 104, 106, 108, 110, 112, 114, 116, 118, and 120 include a reinforcing member that provides additional structural integrity. The reinforcing member can provide several benefits. For example, the reinforcing member provides reinforcement to prevent deformation. The reinforcing member may also facilitate removal of the substrate. The reinforcing member may be located on the surface of the substrate, or it may be embedded within the composition so that the composition forms a matrix about at least a portion of the reinforcing member. The reinforcing member can be made of woven fabrics, nonwoven fabrics, and perforated films. In an embodiment, the reinforcing member is a net (e.g., a polyamide net). In an embodiment, the reinforcing member is a support and the composition is coated on the support.

In an embodiment, the composition includes at least one hydrocolloid in addition to the active agents directed to treat a skin concern. Here, a hydrocolloid is generally any compound that forms a gel with water. The color-coded substrates 102, 104, 106, 108, 110, 112, 114, 116, 118, and 120 may also include a large amount of water. In an embodiment, the color-coded substrates 102, 104, 106, 108, 110, 112, 114, 116, 118, and 120 are applied directly to the skin, without pre-wetting the patch and/or the skin. However, in an alternate embodiment, the color-coded substrates 102, 104, 106, 108, 110, 112, 114, 116, 118, and 120 and/or the skin is pre-wetted prior to application.

Examples of hydrocolloids include cellulose and its derivatives; seaweed extracts; seed extracts; plant exudates; microorganism exudates; fruit extracts; gelling agents of animal origin; synthetic water-soluble gelling polymers; amphiphilic polymers; silicon derivatives; and their mixtures. More specifically, the hydrocolloid may be chosen from:

cellulose and its derivatives such as carboxymethylcellulose, hydroxypropylcellulose, methylcellulose, hydroxypropylmethylcellulose and hydroxyethylcellulose, as well as modified celluloses, especially those modified by grafting of the alkyl group; seaweed extracts such as agar, carrageenans and alginates; seed extracts such as carob gum, guar gum, and modified guar gums, especially those modified by grafting of the alkyl group; plant exudates such as gum arabic, karaya gum, gum tragacanth and gatty gum; microorganism exudates such as xanthan gum; fruit extracts such as pectins; gelling agents of animal origin, such as gelatin and caseinates; synthetic water-soluble gelling polymers such as crosslinked polyacrylic acids, including those crosslinked via an alkyl chain, such as CARBOPOL and PEMULEN from the company Goodrich; silicon derivatives such as synthetic hectorites like the products LAPONITE RD and RDS sold by the company Waverly and aluminum magnesium silicates like the product VEEGUM sold by the company Vanderbilt; polymers such as POLYCARE® sold by the company Rhone-Poulenc under the reference PS-20 and PS-32; and a mixture of these compounds.

In an embodiment, a hydrocolloid chosen from carob gum, xanthan gum, cellulose derivatives, a modified guar gum and mixtures of these compounds may be used in association with the gellan gum. Most particularly xanthan gum, carboxymethylcellulose and modified guar gums are used. In an embodiment, the hydrocolloid associated with the gellan gum is present in an amount ranging from 0.5 to 10% by weight and more preferably from 0.5% to 5% by weight of the total weight of the composition.

In an embodiment, the aqueous phase represents from 60 to 97% by weight of the total weight of the composition and preferably 80 to 95% by weight of the total weight of the composition.

In an embodiment, the composition include compounds including oils, fatty substances, waxes, antioxidants, free-radical scavengers, moisturizers, bleaching agents, liporegulators, anti-acne agents, antiseborrhoeic agents, anti-ageing agents, softeners, anti-wrinkle agents, keratolytic agents, anti-inflammatories, cicatrizing agents, vascular protective agents, antibacterials, antifungals, antiperspirants, deodorants, skin conditioners, desensitizing agents, immunomodulators and nourishing agents, or moisture absorbers (cotton, polyacrylate) and sebum absorbers, or the like.

In embodiments, the color-coded substrates 102, 104, 106, 108, 110, 112, 114, 116, 118, and 120 have a color that is visibly perceived from the exterior and the top side by incorporating synthetic, mineral, and/or organic pigments into the substrate. The pigments may include pigments used in the food sector or in cosmetics, for example, pigments for lipsticks and nail varnishes. By way of example, the pigments may include synthetic pigments or mineral pigments, for example, zirconium oxide or cerium oxide pigments, as well as iron oxide or chromium oxide, and ferric blue, and combinations thereof. Organic pigments can be used, in particular carbon black and barium, strontium, calcium (DC Red No. 7) and aluminum lakes.

Figure 2:
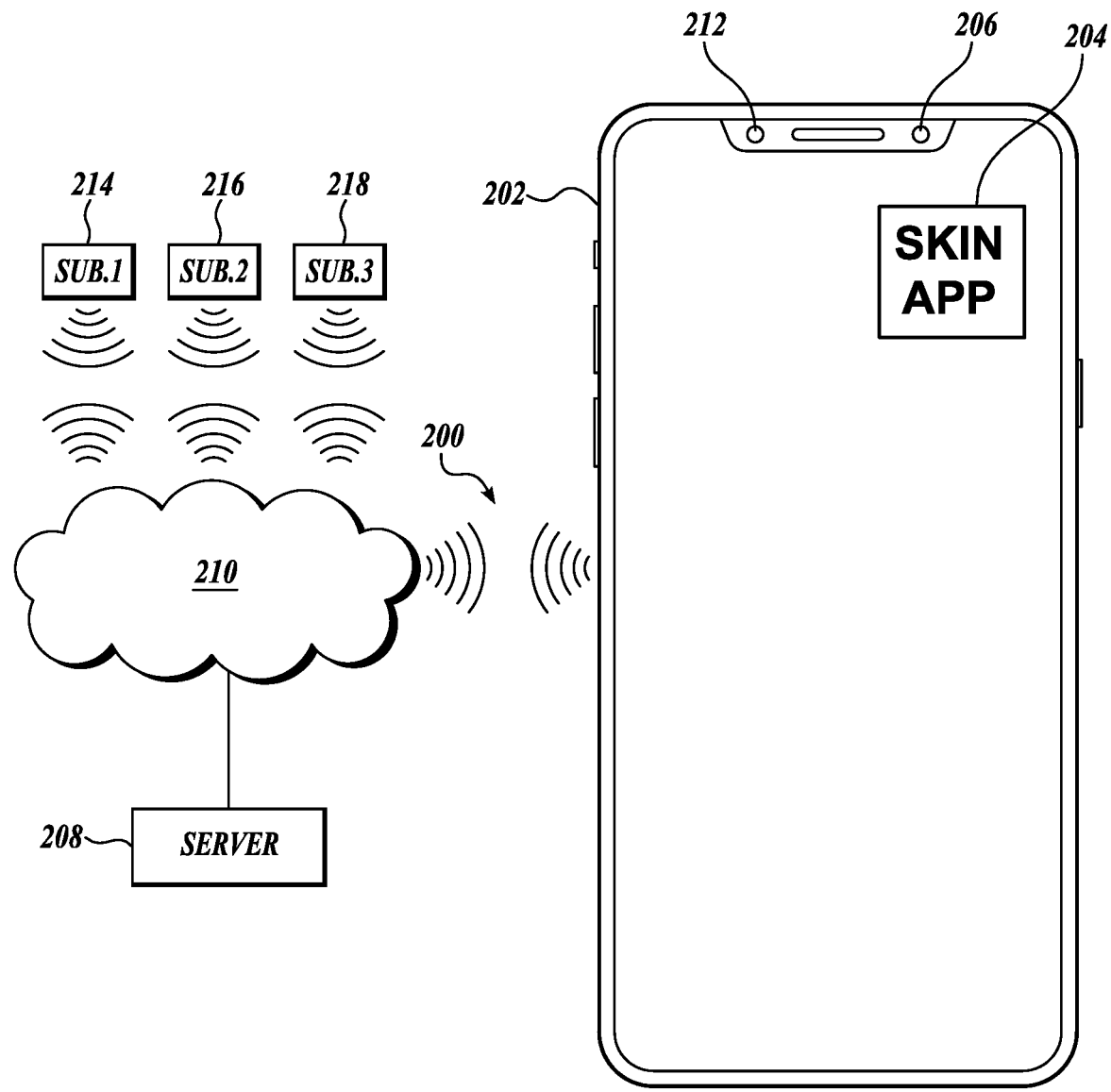
FIG. 2 is a diagrammatical illustration of a mobile computing device including a skin tracking application communicating over a network.

FIG. 2 is a schematic diagram that illustrates one embodiment of a system 200 for tracking a subject's skin concern over time using the color-coded substrates 102, 104, 106, 108, 110, 112, 114, 116, 118, and 120. In the system 200, a subject interacts with a mobile computing device 202. In one embodiment, the mobile computing device 202 is capable of performing the computer-implemented methods designated by the skin app icon 204. The subject may start the computer-implemented methods by touching the icon 204 on a touch-sensitive display of the mobile computing device 202. The computer-implemented methods are further described.

In one embodiment, the mobile computing device 202 is connected to a remote server computer system 208 comprised of one or more server computers via a network, such as the Internet 210. The network may include any suitable networking technology, including but not limited to a wireless communication technology (including but not limited to Wi-Fi, WiMAX, Bluetooth, 2G, 3G, 4G, 5G, and LTE), a wired communication technology (including but not limited to Ethernet, USB, and FireWire), or combinations thereof.

The system 200 may be used by any number of subjects 214, 216, and 218. In the system 200, the various subjects may use mobile computing devices, such as mobile computing device 202, to communicate, share photos, and the like, via text, email, or social media apps.

Figure 3:
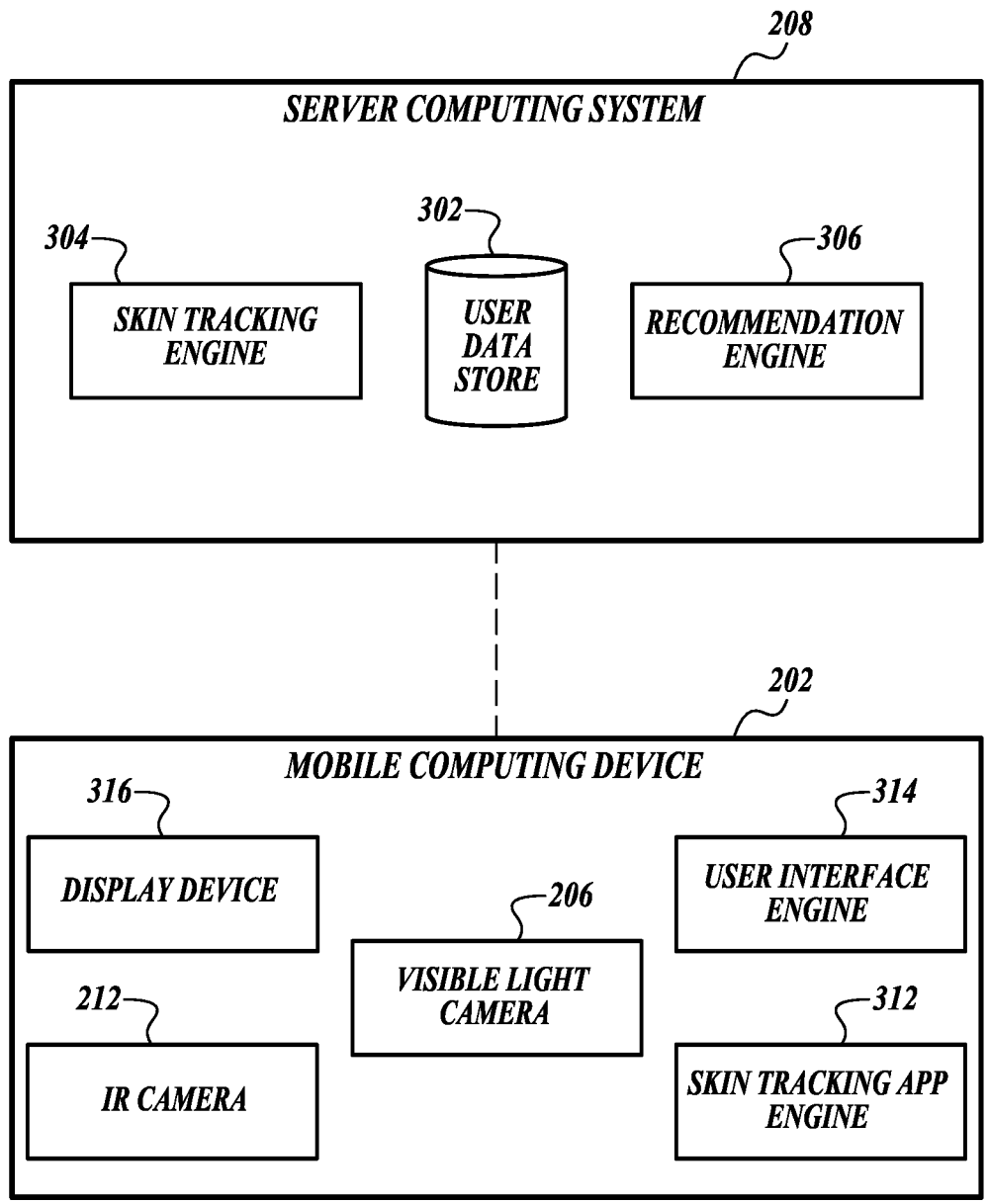
FIG. 3 is a schematic illustration of a computing system.

FIG. 3 is a block diagram that illustrates an embodiment of a system that includes the mobile computing device 202 and the server computing system 208 according to various aspects of the present disclosure.

In one embodiment, the mobile computing device 202 may be a smartphone. In one embodiment, the mobile computing device 202 may be any other type of computing device having the illustrated components, including but not limited to a tablet computing device or a laptop computing device. In one embodiment, the mobile computing device 202 may not be mobile, but may instead be a stationary computing device, such as a desktop computing device. In one embodiment, the illustrated components of the mobile computing device 202 may be within a single housing. In one embodiment, the illustrated components of the mobile computing device 202 may be in separate housings that are communicatively coupled through wired or wireless connections. The mobile computing device 202 also includes other components that are not illustrated, including but not limited to one or more processors, a non-transitory computer-readable medium, a power source, and one or more communication interfaces.

As shown, the mobile computing device 202 includes, at least, a display device 316, a skin tracking application engine 312, an infrared camera 212, a visible light camera 206, and a user interface engine 314.

In an embodiment, the visible light camera 206 of the mobile computing device 202 can differentiate the colors by image processing software or by using a spectrometer for the visible light spectrum. The image processing software can also differentiate wavelengths in the infrared region. In an embodiment, an infrared spectrometer in the infrared camera 212 of the mobile computing device 202 can differentiate the different wavelengths in the infrared spectrum. An infrared camera 212 captures electromagnetic waves in the infrared spectrum, generally defined as being 700 nm to 1 mm. An infrared camera 212 can usually be an attachment onto the mobile computing device 202 and can overlay thermal images onto visible light images obtained from the visible light camera 206. In an embodiment, it may be possible to use a single camera to capture both light in the visible spectrum and the infrared spectrum with the use of filters, for example.

In one embodiment, the display device 316 is an LED display, an OLED display, or another type of display for presenting a user interface. In one embodiment, the display device 316 may be combined with or include a touch-sensitive layer, such that a subject may interact with a user interface presented on the display device 316 by touching the display. In one embodiment, a separate user interface device, including but not limited to a mouse, a keyboard, or a stylus, may be used to interact with a user interface presented on the display device 316.

In one embodiment, the user interface engine 314 is configured to present user interfaces on the display device 316. User interfaces can provide information to the subject, allow the subject to make choices, and generally provides for interacting with the mobile computing device 202. The skin tracking app engine 312 can cause the user interface engine 314 to display a plurality of user interfaces on the display device 316 relating to a computer-implemented method used for the gathering and display of information, including gathering subject specific data.

As described further, the skin tracking app engine 312 can capture images of the skin and analyze the images in either infrared or visible light to determine the skin concerns. Based on the skin concerns detected, the skin tracking app engine 312 can provide recommendations to the subject which color-coded substrates can be used for the particular skin concerns, and perform other monitoring and tracking of the skin concerns over time. In an embodiment, the skin tracking app engine 312 can identify the color-coded substrates while on the skin, tag the skin area relating to a particular skin concern, and then, with the infrared camera takes infrared images to track the skin concern over time. The skin tracking app engine 312 can also perform skin concern analysis and make recommendations.

In an embodiment, the user interface engine 314 displays user interfaces for recommending a personalized set of skincare products depending on the analysis and the results of tracking the skin concerns.

In one embodiment, the server computing system 208 includes one or more computing devices that each include one or more processors, non-transitory computer-readable media, and network communication interfaces that are collectively configured to provide the illustrated components. In one embodiment, the one or more computing devices that make up the server computing system 208 may be rack-mount computing devices, desktop computing devices, or computing devices of a cloud computing service.

As shown, the server computing system 208 includes a user data store 302, a skin tracking engine 304, and a recommendation engine 306. In one embodiment, the server computing system 208 is configured to perform data analytics for determining the skin concern areas from the images captured on the mobile computing device 202 and provide other analysis used by the skin tracking app engine 312.

In one embodiment, the mobile computing device 202 is configured to connect to the server computing system 208 in a cloud computing environment to enable the mobile computing device 202 with the skin tracking app engine 312 to use the computing resources of the server computing system 208. In one embodiment, one, some or all of the components of the user data store 302, skin tracking engine 304 and a recommendation engine 306 can reside in the mobile computing device 202.

In one embodiment, the user data store 302 is configured to store data used by the skin tracking engine 304 of the server computer system 208 and by the skin tracking app engine 312 of the mobile computing device 202. For example, the user data store 302 may store Tables that correspond different colors to different skin concerns, correspond different colors to different active agents, correspond certain shape features to a compatible set, and any other data pertaining to any of the subjects using the skin tracking app. The shades of colors are stored as wavelengths such that an image processor or spectrometer in the visible light camera 206 of the mobile computing device 202 can differentiate the colors by wavelength. The user data store 302 can also store Tables of heat signatures, such as wavelengths in the infrared spectrum that are associated with each of the different skin concerns. An image processor or infrared spectrometer in the infrared camera 212 of the mobile computing device 202 can be able to differentiate the different wavelengths in the infrared spectrum. The user data store 303 may store records for each subject that uses a skin tracking app 204. The records may include the subject's profile including medical or personal records, such as age, weight, skin type, residence, allergies, sensitivities, past or present skin concerns, treatment regimens, past product recommendations, descriptions of lifestyle, and/or other information collected or determined by the system. For example, a subject's profile can include the ongoing skin concerns, the dosages of the substrates being used for treatment of the skin concerns, the daily, weekly, or monthly dosage, and a history of the skin concern over time.

In one embodiment, the user data store 302 may also contain a database of skin types. Skin types may be grouped according to subjective or objective criteria. For example, skin may be characterized as normal, dry, oily, combination, and sensitive, or any combination of two or more factors. In one embodiment, the skin treatment recommendations for a particular skin concern are based on the subject's profile, including skin type and the state or condition of the skin concern.

Further, the skin tracking app engine 312 can determine a color-coded substrate is not the correct area-specific shape for the area of the skin concern. The skin tracking app engine 312 can determine whether a color-coded substrate has an active agent that is not compatible with an agent active of another color-coded substrate. The skin tracking app engine 312 can determine a color-coded substrate is applied to an incorrect area of skin. The skin tracking app engine 312 can determine that a color-coded substrate has an incorrect dosage of active agent. The skin tracking app engine 312 can determine whether the elapsed application time of each color-coded substrate applied to the skin has met or exceeded the pre-determined application time. Based on the determinations, the skin tracking app engine 312 can send a notification to the subject.

In one embodiment, the skin tracking app engine 312 is configured to determine the skin concerns by analyzing a scan or image taken with the mobile computing device 202. In one example, the skin tracking app engine 312 analyzes heat maps captured with the infrared camera to determine each particular skin concern and the area. The heat maps may also allow the skin tracking app engine 312 to determine the severity of the skin concern. In one example, the skin tracking app engine 312 may determine the skin concerns and severity based on visible light images that can detect degrees of light and dark areas, or by detecting absorption of different wavelengths of light. In any case, the skin tracking app engine 312 can determine the specific areas of the skin affected with each skin concern, and can also optionally determine the severity of the skin concern.

In embodiments, the skin tracking app engine 312 can also make other calculations, for example, the skin tracking app engine 312 can determine the distance between the affected skin areas and provide decisions on whether there is a potential incompatibility between active agents.

In embodiments, the skin tracking app engine 312 can be able to determine for each area affected with a skin concern, an area-specific substrate, a color-coded substrate to treat the specific skin concern, a color-coded substrate to deliver a specific dosage of active agent, and color-coded substrates that have active agents that are compatible with each other.

In embodiments, the skin tracking app engine 312 may be configured to process the data acquired by visible light camera 206 to identify the color of the substrates, and then tag the skin area to the particular skin concern. When a color-coded substrate also includes a dosage, the dosage can also be recorded. When an infrared image of the skin area is taken with the infrared camera 212, the skin tracking app engine 312 can determine the skin areas relating to a particular skin concern, make comparisons between the current heat map and a previous heat map, make a determination whether the skin concern is improving, remaining the same, or getting worse. The skin tracking app engine 312 can then make recommendations to reduce or increase the dosage or frequency of application.

In one embodiment, the skin tracking app engine 312 is configured to calculate the subject's skin concerns over time. This comparison can be done on an daily, weekly, monthly, or yearly basis to continually update recommendations for skin treatment substrates.

In one embodiment, the recommendation engine 306 is configured to generate recommendations regarding the dosages and/or frequency of using the substrates.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

"Data store" refers to any suitable device configured to store data for access by any one or more computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art can recognize that separate data stores described herein may be combined into a single data store, and/or a single data store described herein may be separated into multiple data stores. In one embodiment, the user data store 302 is used for storing each subject's profiles, the skin concerns being tracked, and a tracking history for each skin concern. A tracking history may use a value that represents whether the skin concern is improving or getting worse. In one embodiment, the user data store 302 is used for storing the color-coded substrates, the area-specific designation for each color-coded substrate, the dosage of each color-coded substrate, and which active agents are compatible with each other and which are not compatible with each other.

Figure 4:
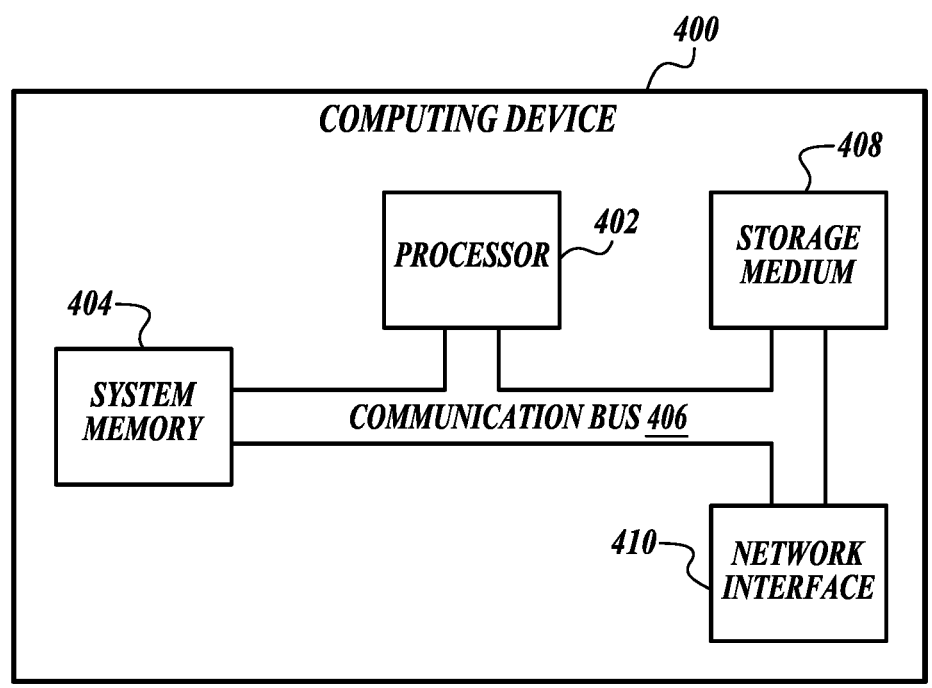
FIG. 4 is a schematic illustration of a mobile computing device.

FIG. 4 is a block diagram that illustrates aspects of an exemplary computing device 400 appropriate for use as a mobile computing device 202 of the present disclosure. While multiple different types of computing devices were discussed above, the exemplary computing device 400 describes various elements that are common to many different types of computing devices. While FIG. 4 is described with reference to a mobile computing device, the description below is applicable to servers, personal computers, mobile phones, smart phones, tablet computers, embedded computing devices, and other devices that may be used to implement portions of embodiments of the present disclosure. Moreover, those of ordinary skill in the art and others can recognize that the computing device 400 may be any one of any number of currently available or yet to be developed devices.

In its most basic configuration, the computing device 400 includes at least one processor 402 and a system memory 404 connected by a communication bus 406. Depending on the exact configuration and type of device, the system memory 404 may be volatile or nonvolatile memory, such as read only memory ("ROM"), random access memory ("RAM"), EEPROM, flash memory, or similar memory technology. Those of ordinary skill in the art and others can recognize that system memory 404 typically stores data and/or program modules that are immediately accessible to and/or currently being operated on by the processor 402. In this regard, the processor 402 may serve as a computational center of the computing device 400 by supporting the execution of instructions.

As further illustrated in FIG. 4, the computing device 400 may include a network interface 410 comprising one or more components for communicating with other devices over a network. Embodiments of the present disclosure may access basic services that utilize the network interface 410 to perform communications using common network protocols. The network interface 410 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 410 illustrated in FIG. 4 may represent one or more wireless interfaces or physical communication interfaces described and illustrated above with respect to particular components of the computing device 400.

In the exemplary embodiment depicted in FIG. 4, the computing device 400 also includes a storage medium 408. However, services may be accessed using a computing device that does not include means for persisting data to a local storage medium. Therefore, the storage medium 408 depicted in FIG. 4 is optional. In any event, the storage medium 408 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 404 and storage medium 408 depicted in FIG. 4 are merely examples of computer-readable media.

Suitable implementations of computing devices that include a processor 402, system memory 404, communication bus 406, storage medium 408, and network interface 410 are known and commercially available. For ease of illustration and because it is not important for an understanding of the claimed subject matter, FIG. 4 does not show some of the typical components of many computing devices. In this regard, the computing device 400 may include input devices, such as a keyboard, keypad, mouse, microphone, touch input device, touch screen, tablet, and/or the like. Such input devices may be coupled to the computing device 400 by wired or wireless connections including RF, infrared, serial, parallel, Bluetooth, Bluetooth low energy, USB, or other suitable connections protocols using wireless or physical connections. Similarly, the computing device 400 may also include output devices such as a display, speakers, printer, etc. Since these devices are well known in the art, they are not illustrated or described further herein.

In an embodiment, FIGS. 3 and 4 illustrate a skincare system components 202, 208, 400 comprises circuitry configured to determine a color and geometry of a color-coded substrate responsive to one or more inputs indicative of a presence or absence of a skin concern; circuitry configured to tag or classify digital images based on a color and geometry of one or more color-coded substrates applied to the area of skin present in the image; circuitry configured to predicted a skin concern outcome responsive to a tag or classification indicative of a color and geometry of a color-coded substrate applied to the area of skin.

The skincare system components 202, 208, 400 further comprises circuitry configured to generate a digital representation of the area of skin including one or more instances of the predicted skin concern outcome.

The skincare system components 202, 208, 400 further comprises circuitry configured to generate an alert associated with a time to apply or remove a color-coded substrate, the alert including color and geometry information associated with the color-coded substrate for application or removal.

The skincare system 202, 208, 400 wherein the circuitry is configured to tag or classify the digital images based on a color and geometry of the one or more color-coded substrates applied to the area of skin present in the image further includes circuitry configured to tag or classify digital images with treatment or active agent information based on a color and geometry of a color-coded substrate applied to the area of skin present in the image.

Figure 5:
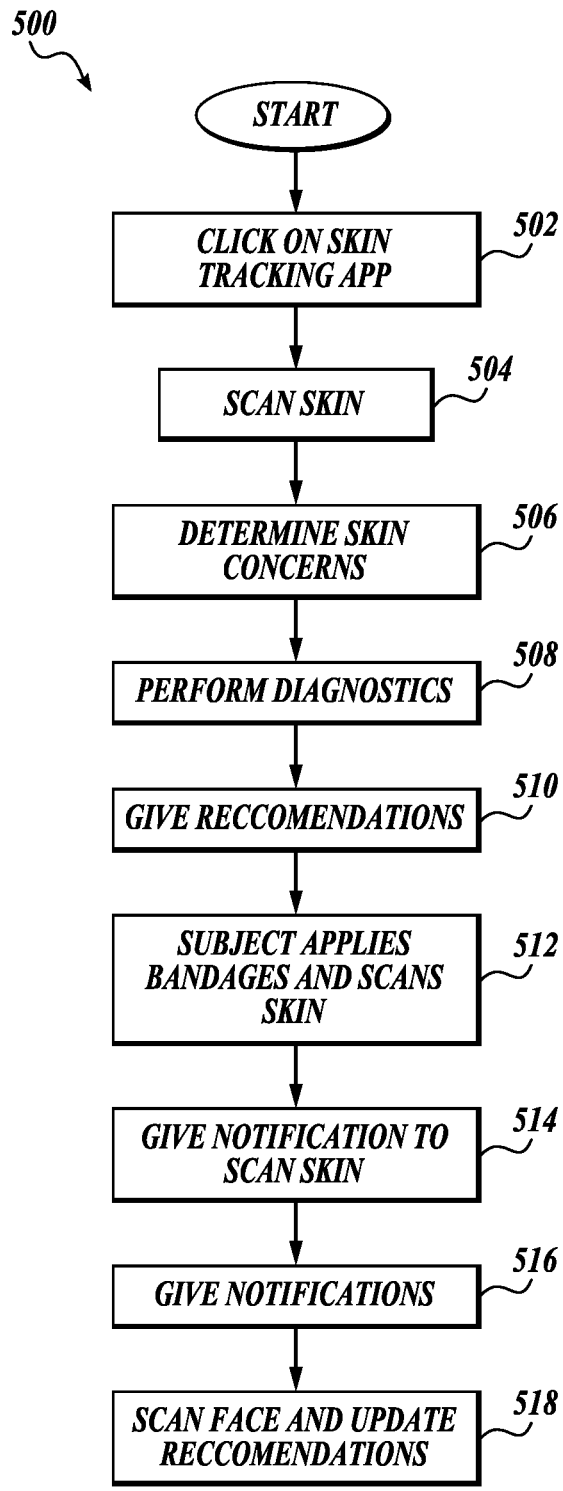
FIG. 5 is a step diagram of one example of a skin tracking application.

FIG. 5 is a flow diagram that illustrates one embodiment of a computer-implemented method 500 of identifying and treating skin concerns using the example color-coded substrates 102, 104, 106, 108, 110, 112, 114, 116, 118, and 120.

In one embodiment, the method 500 may be implemented, in one example, by the mobile computing device 202 alone or in combination with one or more server computing system 208. The blocks of the computer-implemented method can be performed by the skin tracking app engine 312, skin tracking engine 304, recommendation engine 306, user interface engine 314 communicating with each other and with the user data store 302. In embodiments, the skin tracking app engine 312 is configured work in combination with the server's skin tracking engine 304 to use the resources of the server computing system 208. In one embodiment, the method may be performed in part by the mobile computing device 202 and in part by the remote server computer system 208. In one embodiment, the method may be performed by the mobile computing device 202.

The computer-implemented method may start by clicking on the skin tracking app icon 204 on the display of the mobile computing device 202 to open the skin tracking app engine 312 in block 502. After block 502, the method proceeds to block 504.

In block 504, the subject uses the mobile computing device 202 to scan the skin or face using a camera, such as visible light camera 206 or infrared camera 212. From block 504, the method proceeds to block 506.

In block 506, the skin tracking app engine 312 uses the image or images to determine facial features and skin concerns affecting the skin. The skin tracking app engine 312 can determine the skin concern and the area of the face affected by the skin concern. In one example, infrared images are used to generate heat maps, wherein each different skin concern has a different heat signature next to normal skin, and therefore, the skin concerns can be determined by the unique heat signature. In one example, absorption of visible light or wavebands of visible is different for different skin concerns, and therefore, the specific skin concerns can be detected by measuring the reflectance of light or a particular wavelength of light from the skin.

Figure 7:
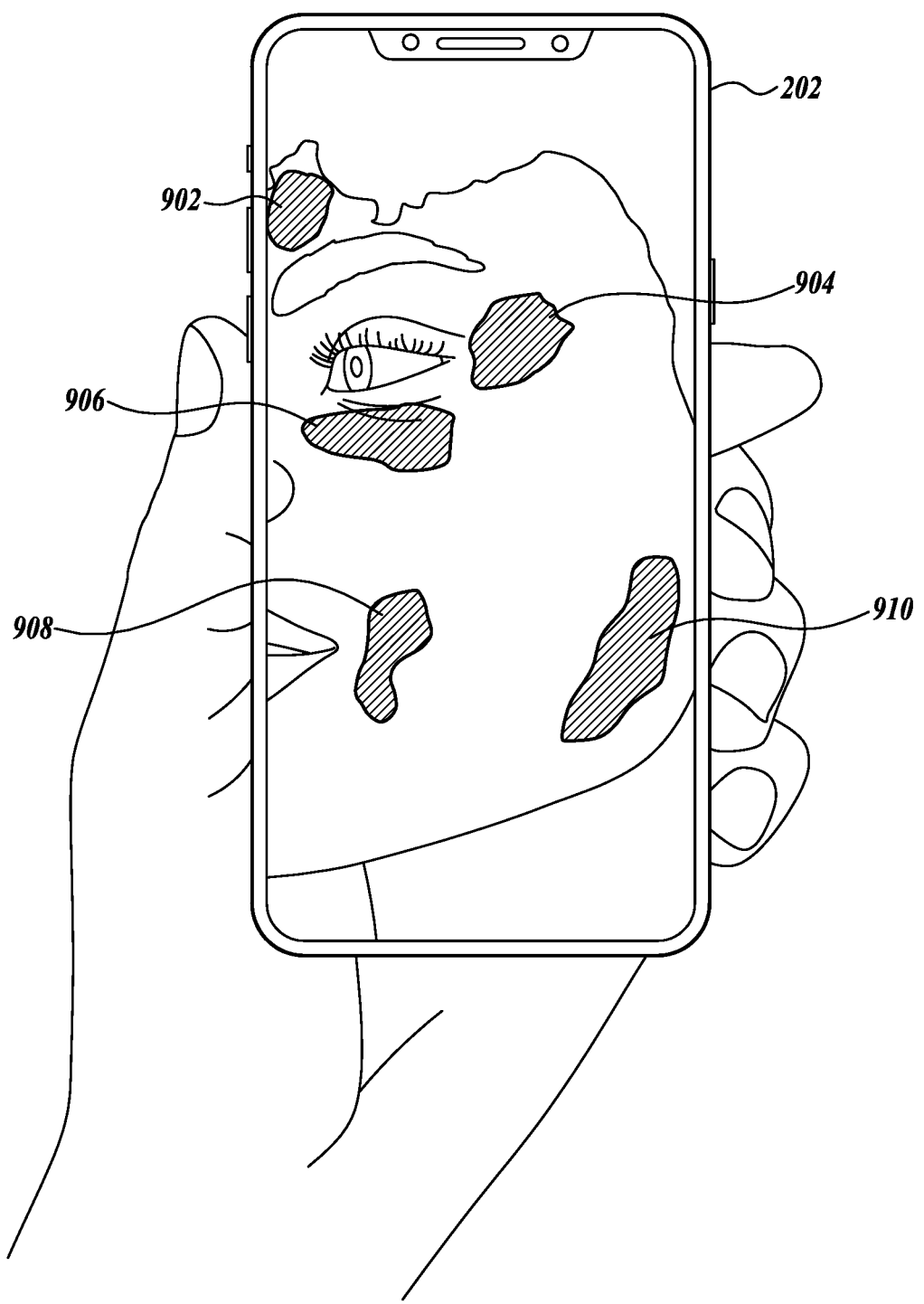
FIG. 7 is a diagrammatical illustration of a scan taken on a mobile computing device for detecting skin concerns.

Referring to FIG. 7, one example of a scan created on the mobile computing device 202 includes an image of a subject's face overlaid with areas identified as one or more skin concerns. For example, the glabella area 902 is indicated as acne, the corner eye area 904 is indicated as wrinkles, the lower eye or cheekbone area 906 is indicated as wrinkles, the corner mouth area 908 is indicated as wrinkles, and the cheek or jawline area 910 is indicated as post inflammatory hyper-pigmentation. From block 606, the method proceeds to block 508.

In block 508, after having identified the skin concerns, severity of skin concerns and the facial areas, the skin tracking app engine 312 can perform diagnostics to make treatment recommendations. The skin tracking app engine 312 has acquired the personal and historical treatment information from the user data store 302. The skin tracking app engine 312 may first determine whether the subject has any allergies or is sensitive to any active agents, which is used to determine which compatible set of color-coded substrates 102, 104, 106, 108, 110, 112, 114, 116, 118, and 120 to recommend. For example, the skin tracking app engine 312 can select either one of the color-coded substrates of the top or bottom row of FIG. 1. However, it is possible to have more than two compatible sets, the illustrated sets are meant to be examples. Each compatible set of color-coded substrates is provided in the area-specific shapes, and each area-specific substrate can be provided in every color code with the corresponding active agent for treating every skin concern and dosage for treating severe or mild of the skin concerns. From the facial scan, the skin tracking app engine 312 is able to determine the skin concern and optionally the severity and make an association to the specific area of the face. The skin tracking app engine 312 is able to determine which shape of area-specific color-coded substrate to recommend, and in addition, the skin tracking app engine 312 is able to determine the color code of the area-specific substrate to recommend for the particular skin concern and the dosage. From block 508, the method proceeds to block 510.

In block 510, the user interface engine 314 presents the recommendations to the subject via, for example, in the form of graphics or text. A graphic may be presented which shows the facial image overlaid with the area-specific color-coded substrates on the areas where to apply them. The user interface engine 314 may also present instructions or helpful links. From block 510, the method proceeds to block 512.

Figure 8:
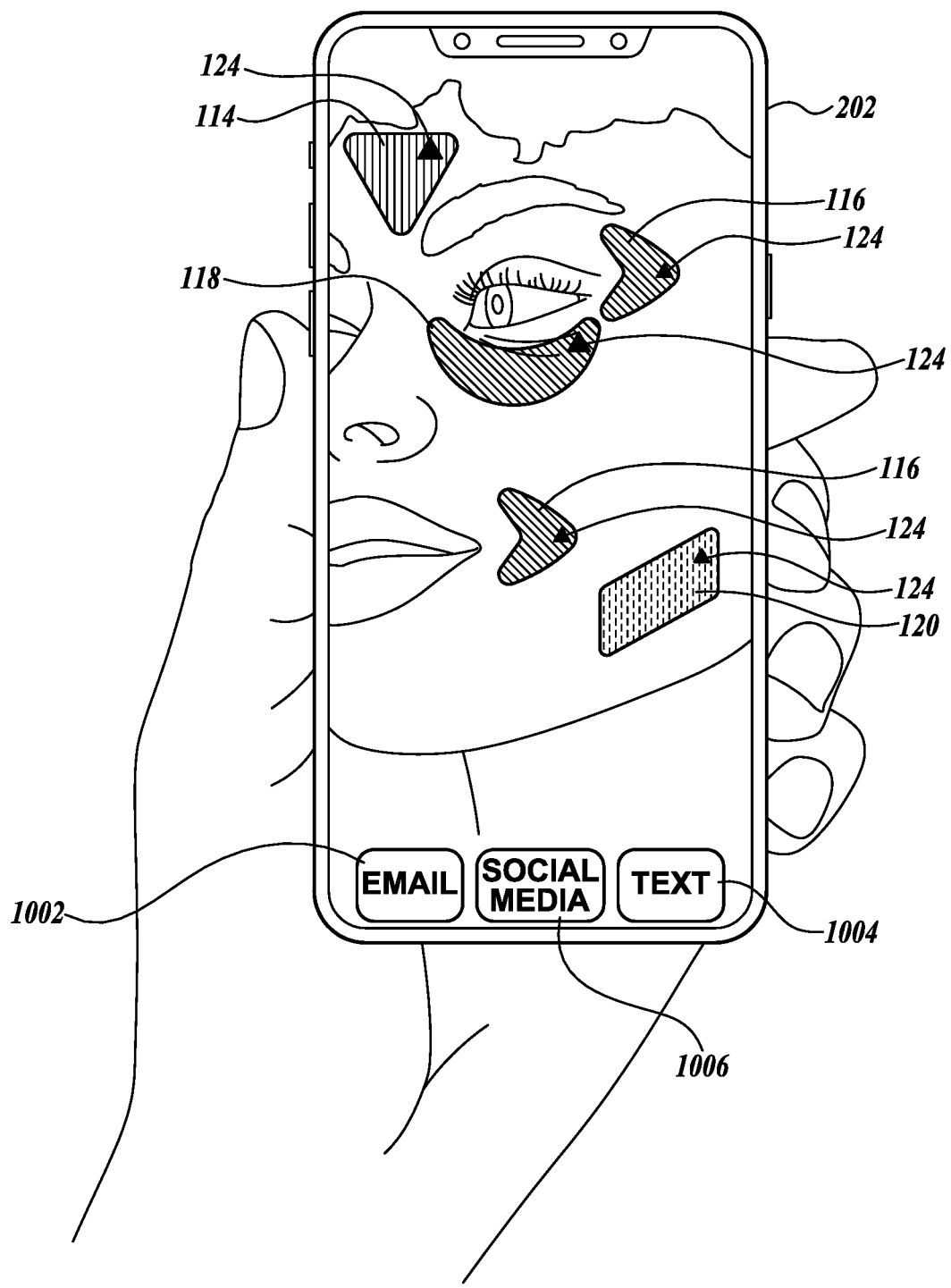
FIG. 8 is a diagrammatical illustration of a scan taken on a mobile computing device for detecting color-coded and area-specific color-coded substrates.
Figure 10:
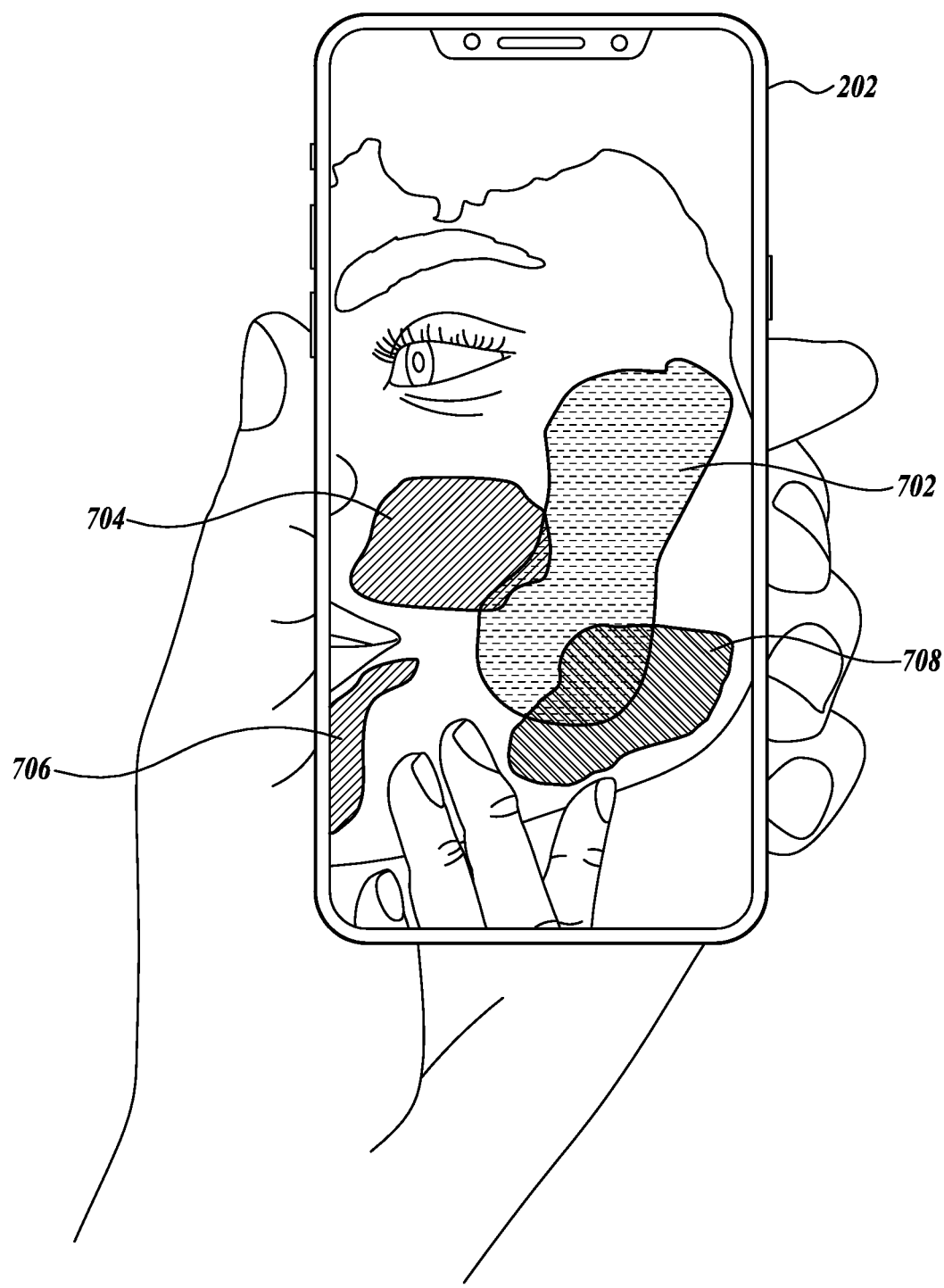
FIG. 10 is a diagrammatical illustration of a heat map taken on a mobile computing device.

In block 512, the subject applies the recommended color-coded substrates. The subject may take another image with the mobile computing device 202. FIG. 8 is an example of an image taken by the subject using the mobile computing device 202 after application of the color-coded substrates 102, 104, 106, 108, 110, 112, 114, 116, 118, and 120 according to the skin tracking app engine 312 recommendations. In FIG. 10, the glabella area is covered by the glabella specific color-coded substrate 114 in pink for treatment of acne. The corner eye area is covered by the corner eye specific color-coded substrate 116 in green for wrinkles. The under eye or cheekbone area is covered by the under eye specific color-coded substrate 118 in green for wrinkles. The corner mouth area is covered by the corner mouth specific color-coded substrate 116 in green for wrinkles. The cheek or jawline area is covered by the jawline specific color-coded substrate 120 in violet for post inflammatory hyperpigmentation.

In FIG. 8, it is seen that color-coded substrates in specific shapes can be pleasing to look at, can be amusing for the subject and others, or can represent a form of expression or represent a mood of subject. In an example, the color-coded substrates can be seen as wearable art that a subject may want to share with other subjects. In an example, the skin tracking app engine 312 can allow the subject to share the image via email 1002, text 1004, or post to any social media 1006. From block 512, the method proceeds to block 514.

Figure 9:
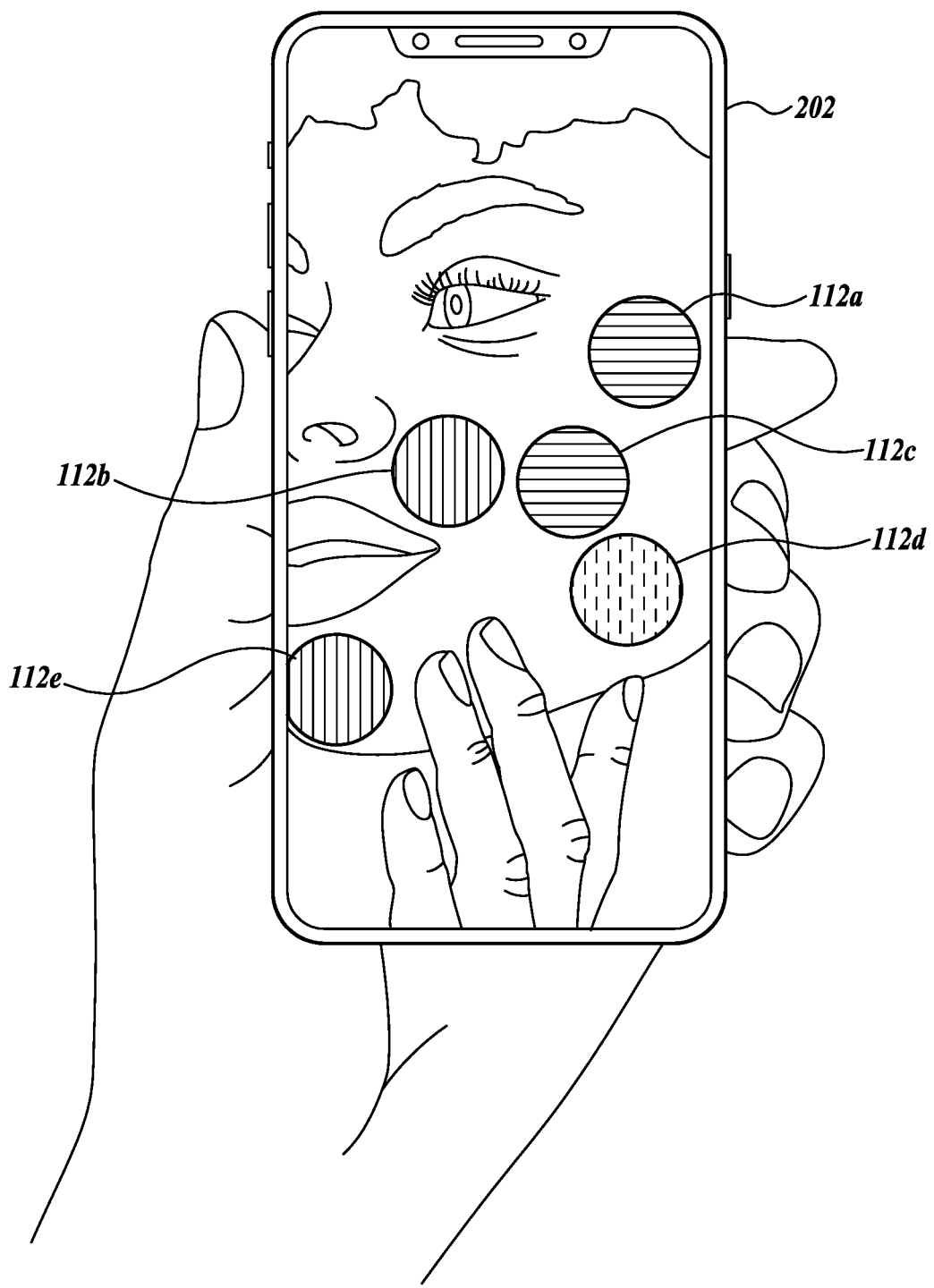
FIG. 9 is a diagrammatical illustration of an image taken on a mobile computing device.

In block 514, the skin tracking app engine 312 can perform diagnostics from the image in FIG. 9 to confirm that the correct color-coded substrates 102, 104, 106, 108, 110, 112, 114, 116, 118, and 120 are in the correct area and are compatible with each other. In one example, the skin tracking app engine 312 recognizes the color code of each color-coded substrate, assigns the skin concern associated with the color code, and then compares the assigned skin concern to the skin concerns detected from the earlier scan of FIG. 7. When the assigned skin concern does not match the skin concern detected earlier for the area, the skin tracking app engine 312 can send a notification to the subject that a color-coded substrate is matched with the wrong skin concern.

In one example, the skin tracking app engine 312 recognizes the color code of each color-coded substrate, assigns the dosage associated with the color code, and then compares the assigned dosage to the dosage recommended from the earlier scan of FIG. 7. When the assigned dosage does not match the dosage recommended earlier, the skin tracking app engine 312 can send a notification to the subject that the dosage of a color-coded substrate does not match the recommended dosage.

In one example, the skin tracking app engine 312 recognizes the shape of each color-coded substrate, assigns the specific area associated with the shape of the color-coded substrate, and then compares the assigned area to the skin concern area detected from the earlier scan of FIG. 7. When the assigned shape does not match the skin concern area detected earlier, the skin tracking app engine 312 can send a notification to the subject that a color-coded substrate, while being of the correct color code, is not of the correct area-specific shape.

In one example, the skin tracking app engine 312 recognizes a shape feature or symbol that designates compatibility. For example, the color-coded substrates in FIG. 8 do not include an angle in the shape, therefore, the skin tracking app engine 312 is able to confirm that the active agents in the color-coded substrates are compatible. In another example, the color-coded substrates in FIG. 8 all include the triangle symbol 124 indicating that the color-coded substrates are compatible. The color-coded substrates in FIG. 9 can be selected from among the compatibility set shown in the bottom row of FIG. 1. When either a shape feature or a symbol indicates that a color-coded substrate is not from a compatibility set, the skin tracking app engine 312 may send a notification to the subject.

In another example, it can be possible to include color-coded substrates of different compatibility sets and the skin tracking app engine 312 can check the proximity of any two color-coded substrates that are not compatible to determine whether a distance between non-compatible color-coded substrates is acceptable. In a case where two or more color coded substrates are not compatible with each other based on a proximity limit, the skin tracking app engine 312 can send a notification to the subject. From block 514, the method proceeds to block 516.

In block 516, the skin tracking app engine 312 assigns a time that each of the color-coded substrates 102, 104, 106, 108, 110, 112, 114, 116, 118, and 120 is first applied, and thereafter keeps track of the time that each color-coded substrate remains on the skin. The skin tracking app engine 312 has stored in memory a pre-determined application time of each color-coded substrate representing a treatment time of the active agents. The skin tracking app engine 312 determines whether the elapsed application time of each color-coded substrate applied to the skin has met or exceeded the pre-determined application time. When the skin tracking app engine 312 determines that the elapsed application time on the skin of a color-coded substrate is equal to or greater than the pre-determined application time, skin tracking app engine 312 can send a notification to the subject that the color-coded substrate can be removed. The user interface engine 314 can display graphical images which of the color-coded substrates should be removed, such as an image similar to FIG. 8 where the color-coded substrate to be removed is blinking. Also, after any scan, the skin tracking app engine 312 can determine that a color-coded substrate has been removed prior to expiration of the pre-determined application time, and the skin tracking app engine 312 can send a notification to the subject that a color-coded substrate has been removed earlier than the recommended application time. From block 516, the method enters block 518.

In block 518, the subject can scan the face once again after removal of one or more of the color-coded substrates. Generally, a subject may scan the face at any time before, during, or after application of one or more of the color-coded substrates 102, 104, 106, 108, 110, 112, 114, 116, 118, and 120. The skin tracking app engine 312 is able to determine the stage of treatment of each skin concern, and bases recommendations, notifications, on determining the stage of treatment of each skin concern. It is possible that some skin concerns appear and disappear over time, and the skin tracking app engine 312 can be able to determine the start of each skin concern to the end of the skin concern. The skin tracking app engine 312 can be able to manage each skin concern regardless of the stage, i.e., while some skin concerns can be ending, other new skin concerns may be appearing, and the skin tracking app engine 312 can be configured to apply different rules for ongoing and new skin concerns. In embodiments, after any scan, the skin tracking app engine 312 can determine whether new skin concerns have appeared and also give notifications of ongoing skin concerns.

Figure 6:
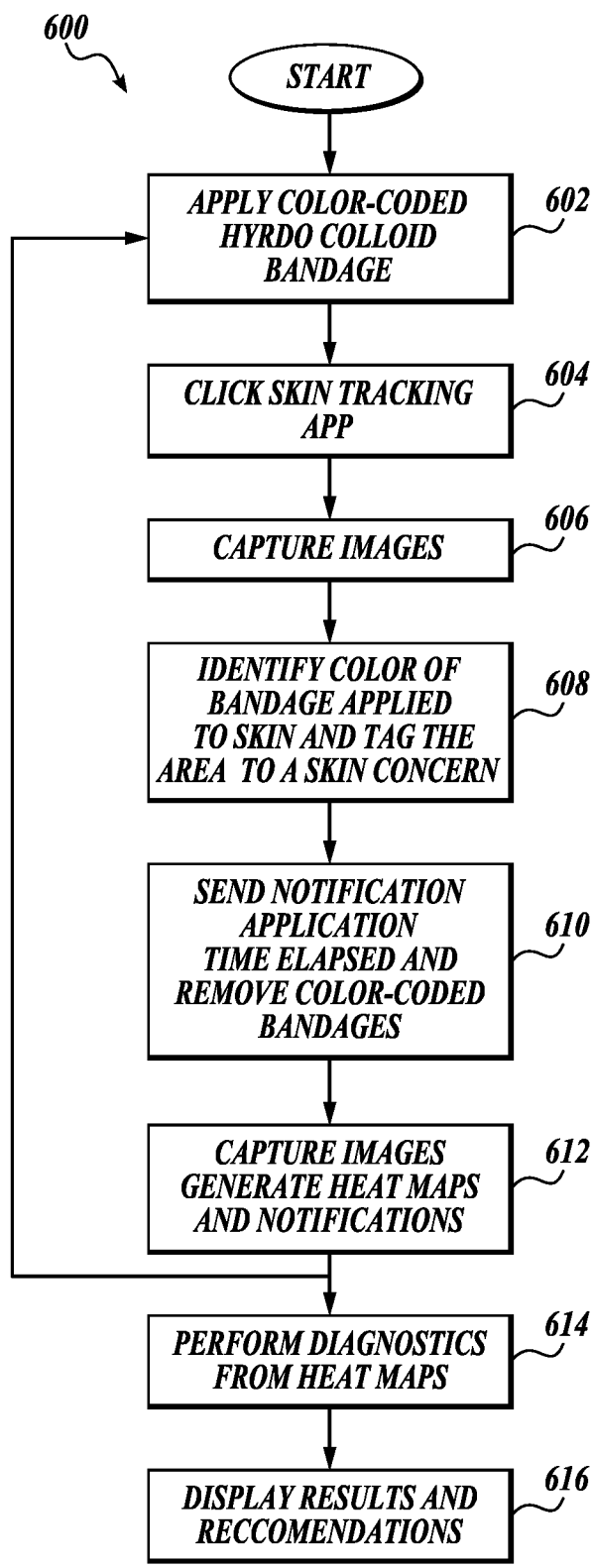
FIG. 6 is a step diagram of one example of a skin tracking application.

FIG. 6 is a flow diagram that illustrates one embodiment of a computer-implemented method 600. FIG. 6 illustrates that the skin tracking app engine 312 can operate according to a different sequence. For example, the skin tracking app engine 312 does not require a scan to identify the skin concerns first, but instead may rely on the subject placing the color-coded substrates 102, 104, 106, 108, 110, 112, 114, 116, 118, and 120 on first in the correct skin concern areas. The skin tracking app engine 312 can later verify whether or not the color-coded substrates placed by the subject are in the correct area, the correct shape, the correct dosage, and for the correct skin concern.

In the method of FIG. 6, after the subject places color-coded substrates on the areas with skin concerns, in block 602, the subject can click on the skin tracking app icon 204 on the mobile computing device 202 to start the skin tracking app engine 312, in block 604. Upon starting, the skin tracking app engine 312 may send a notification to the subject to take an image, and the subject captures an image, in block 606.

In block 606, a subject can capture a visible light image of the areas of skin being covered by the color-coded substrates 102, 104, 106, 108, 110, 112, 114, 116, 118, and 120 with the visible light camera 206 on the mobile device 202. The aim of a visible light image is to tag the areas of skin with the skin concern based on the color of the color-coded substrates applied on the skin. From block 606, the method proceeds to block 608.

In block 608, the skin tracking app engine 312 can process the visible light image to determine the color code of the color-coded substrates applied on the skin. The skin tracking app engine 312 can tag the area of skin with the particular skin concern associate with the color code. If the color-coded substrates indicate a dosage, the skin tracking app engine 312 can also save the dosage associated with the substrates.

FIG. 9 illustrates a visible light image captured by the mobile computing device 202. The image shows the subject's face and color-coded substrates 112*a*, 112*b*, 112*c*, 112*d*, and 112*e* applied to the skin. The color code of the color-coded substrate can indicate a particular active to treat a particular skin concern and a dosage. For example, substrate 112*a* may indicate dark spots and a low dosage, substrate 112*c* may indicate dark spots and a high dosage, substrate 112*b* may indicate acne at a low dosage, substrate 112*e* may indicate acne at a high dosage, and substrate 112*d* may indicate PIH. Different colored substrates may represent different skin concerns, while different shades of the same color may indicate the same skin concern, but, have different dosages. The skin tracking app engine 312 is able to determine from the location of the color-coded substrate the area of skin associated with each color-coded substrate. From block 608, the method proceeds to block 610.

In block 610, the skin tracking app engine 312 determines how much time is elapsed from the time the color-coded substrates have been applied on the skin. The skin tracking app engine 312 determines when an elapsed application time of the color-coded substrate exceeds a pre-determined application time and sends a notification to remove the color-coded substrate. The predetermined application time is a recommended time that any given active agent at a particular dosage should be left applied to the skin. Once the skin tracking app engine 312 determines the elapsed application time exceeds the pre-determined application time, the skin tracking app engine 312 may send a notification indicating that the subject may remove the substrates. From block 610, the method enters block 612.

In block 612, after one or more of the substrates are removed, the subject captures an infrared image of the same skin area using the infrared camera 212 or other camera capable of being used to determine skin concerns. In block 612, the skin tracking app engine 312 can process the IR image to determine the extent of the areas pertaining to each skin concern and also the severity or lack of severity of the skin concern. Image processing may include generating a heat map wherein different wavelengths may indicate different skin concerns and normal skin via image processing software.

FIG. 10 is an example of a heat map superimposed on the visible light image to display the extent and severity level of each of the skin concerns. The extent of a skin concern may be delineated by a line, while the severity of the skin concern may be designated by a different heat signature. The heat signature of a skin concern may be different to the heat signature of surrounding "normal" skin without any skin concerns. For example, the area 702 designates the extent and severity of dark spots, the areas 704 and 706 designate the extent and severity of acne, and the area 708 designates the extent and the severity of PIH.

Further, in block 612, the skin tracking app engine 312 can determine whether a color-coded substrate has an active agent that is not compatible with an active agent of another color-coded substrate. The skin tracking app engine 312 can determine a color-coded substrate is applied to an incorrect area of skin. The skin tracking app engine 312 can determine a color-coded substrate has an incorrect dosage of active agent for the area it is being applied. The skin tracking app engine 312 can determine a color-coded substrate is an incorrect shape for the area it is being applied.

In one embodiment, for the first iteration of the method 600, the first heat map generated in block 612 can be designated as the baseline case. From block 612, after the first iteration, the method can return to block 602 where the subject applies a second color-coded substrate on the skin concern. After the second and subsequent applications of color-coded substrates to the affected skin concerns, the heat maps generated after the second and subsequent applications can be compared and analyzed against each other in block 614.

In block 614, the skin tracking app engine 312 can perform diagnostics from the heat maps. For example, the area of the skin concern can be determined and compared to the previous heat map to determine whether the skin concern is increasing or diminishing. The severity of the skin concern can be determined, for example, by the heat signature compared to the heat signature of the normal skin. The severity of the skin concern can also be compared to the previous heat map to determine not only whether the area of skin concern is increasing or decreasing, but to determine also whether the severity of the skin concern is increasing or decreasing. From block 614, the method enters block 616.

In block 616, the subject may be presented with a user interface via the user interface engine 314 providing for various options. For example, the subject may have the option to display on the mobile computing device an image of the heat map, or a processed image of the most recent heat map superimposed over the visible light image to show the extent of the various skin concerns. The images may be saved according to date, and the subject may recall any previous image to compare to the most recent image. The subject may also review the treatment regimen, such as how long the skin concern has been treated, the dates of treatment, and the dosages. The user interface may also provide numerical values to characterize the increase or decrease of the extent of the skin concern. The user interface may also provide numerical values to characterize the increase or decrease in the severity of the skin concern. The user interface engine 314 can display helpful graphs, data, information, warnings, chat links, informative links, and help links. The recommendation engine 306 may display the recommendation for the next treatment and the dosage, or may recommend a new color-coded substrate. The recommendation engine 306 may also provide notifications when the next treatment is due and the expiration of the treatment to remove the substrate. Additionally, the user interface engine 314 can be used to make a purchase of any products related to the color-coded substrates or other products.

In an embodiment, a computer-implemented method 500, 600 of tracking skin concerns, comprises determining, by a computing device, a skin concern and an area of skin affected by the skin concern; and determining, by the computing device, a color-coded substrate to apply to the area of skin.

In an embodiment, the color-coded substrate includes at least one hydrocolloid and an active agent, and the skin concern includes one or more of acne, wrinkles, dark spots, and post inflammatory hyper-pigmentation.

In an embodiment, the method further comprises, recommending, by the computing device, to apply the color-coded substrate in the area of skin affected by the skin concern.

In an embodiment, the method further comprises, determining, by the computing device, a shape of an area-specific color-coded substrate that conforms to the area of skin.

In an embodiment, the method further comprises, determining, by the computing device, a color-coded substrate has an active agent that is not compatible with an agent active of another color-coded substrate.

In an embodiment, the method further comprises, determining, by the computing device, a color-coded substrate is applied to an incorrect area of skin.

In an embodiment, the method further comprises, determining, by the computing device, a color-coded substrate having an incorrect dosage of active agent is applied to the area of skin.

In an embodiment, the method further comprises, determining, by the computing device, an elapsed application time of the color-coded substrate exceeds a pre-determined application time, and the computing device sends a notification to remove the color-coded substrate.

In an embodiment, the method further comprises, determining, by the computing device, a skin concern is increasing or decreasing by comparing a first heat map to a second heat map.

In an embodiment, one or more computing devices 202, 208 are configured to determine a skin concern and an area of skin affected by the skin concern; and determine a color-coded substrate to apply to the area of skin.

The one or more computing devices 202, 208 comprise a visible light camera or an infrared camera or both a visible light camera and an infrared camera.

The one or more computing devices 202, 208 are configured to recommend to apply the color-coded substrate in the area of skin affected by the skin concern.

The one or more computing devices 202, 208 are configured to determine a shape of an area-specific color-coded substrate that conforms to the area of skin.

The one or more computing devices 202, 208 are configured to determine a color-coded substrate has an active agent that is not compatible with an agent active of another color-coded substrate.

The one or more computing devices 202, 208 are configured to determine a color-coded substrate is applied to an incorrect area of skin.

The one or more computing devices 202, 208 are configured to determine a color-coded substrate having an incorrect dosage of active agent is applied to the area of skin.

The one or more computing devices 202, 208 are configured to determine an elapsed application time of the color-coded substrate exceeds a pre-determined application time, and the computing device sends a notification to remove the color-coded substrate.

The one or more computing devices 202, 208 are configured to determine a skin concern is increasing or decreasing by comparing a first heat map to a second heat map.

In an embodiment, a computer-implemented method 500, 600 of tracking skin concerns, comprises determining, by a computing device, a color of a color-coded substrate applied to an area of skin; determining, by the computing device, a skin concern associated with the color of the color-coded substrate; and determining, by the computing device, an area of skin affected with the skin concern.

In an embodiment, a skincare system 202, 208, 400 comprises circuitry configured to determine a color and geometry of a color-coded substrate responsive to one or more inputs indicative of a presence or absence of a skin concern; circuitry configured to tag or classify digital images based on a color and geometry of one or more color-coded substrates applied to the area of skin present in the image; circuitry configured to predicted a skin concern outcome responsive to a tag or classification indicative of a color and geometry of a color-coded substrate applied to the area of skin.

The skincare system 202, 208, 400 further comprises circuitry configured to generate a digital representation of the area of skin including one or more instances of the predicted skin concern outcome.

The skincare system 202, 208, 400 further comprises circuitry configured to generate an alert associated with a time to apply or remove a color-coded substrate, the alert including color and geometry information associated with the color-coded substrate for application or removal.

The skincare system 202, 208, 400 wherein the circuitry is configured to tag or classify the digital images based on a color and geometry of the one or more color-coded substrates applied to the area of skin present in the image further includes circuitry configured to tag or classify digital images with treatment or active agent information based on a color and geometry of a color-coded substrate applied to the area of skin present in the image.

A system of color-coded substrates 102, 104, 106, 108, 110, 112, 114, 116, 118, and 120 for application to skin for the treatment of skin concerns, comprises a first color-coded substrate including an active agent for treatment of a first skin concern; and a second color-coded substrate including an active agent for treatment of a second skin concern, a color code of the first color-coded substrate is different to the color code of the second color-coded substrate.

The system of color-coded substrates comprises a plurality of color-coded substrates having area-specific shapes in the first color code and a plurality of color-coded substrates having area-specific shapes in the second color code.

The system of color-coded substrates comprises a plurality of color-coded substrates having different dosages of the first active agent and a plurality of color-coded substrates having different dosages of the second active agent.

The system of color-coded substrates comprises a plurality of color-coded substrates, each color-coded substrate having a shape feature indicating active agents in the plurality of color-coded substrates are compatible.

The system of color-coded substrates comprises a plurality of color-coded substrates, each color-coded substrate having a symbol indicating active agents in the plurality of color-coded substrates are compatible.

The system of color-coded substrates comprises a plurality of color-coded substrates, each having a different dosage of the first active agent, wherein each of the plurality of color-coded substrates having a different dosage have a different color code.

The system of color-coded substrates comprises a plurality of color-coded substrates provided in area-specific shapes for each of the different dosages of the first active agent.

The system of color-coded substrates has the first color-coded substrate further comprising a composition including at least one hydrocolloid.

The system of color-coded substrates comprises the first color-coded substrate having an adhesive on one side.

The system of color-coded substrates comprises a plurality of color-coded substrates having area-specific shapes include at least one angle formed from two straight lines.

The system of color-coded substrates comprises a plurality of color-coded substrates having area-specific shapes include no angles formed from two straight lines.

The system of color-coded substrates has the first color-coded substrate and the second color-coded substrate including an active agent for the treatment of one of acne, pigmentation, dark spots, wrinkles, or post inflammatory hyper-pigmentation.

The system of color-coded substrates comprises a plurality of color-coded substrates having area-specific shapes selected from a circle, square, triangle, chevron, crescent, and parallelogram.

The system of color-coded substrates includes bandages, patches, carriers, or tapes.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method of tracking skin concerns, the method comprising:
   determining, by a computing device, a skin concern and an area of skin affected by the skin concern; and
   determining, by the computing device, a color-coded substrate to apply to the area of skin, the color-coded substrate is selected from a plurality of color-coded substrates, wherein each color-coded substrate includes a reinforcing member coated with a composition including at least one hydrocolloid and an active agent, wherein each color-coded substrate has a color, an area-specific shape, and a shape feature, wherein,
   each different color indicates a different active agent,
   each area-specific shape conforms to a specific area of a face or skin, and
   color-coded substrates having a same shape feature indicates compatibility of active agents among color-coded substrates having different colors.

2. The computer-implemented method of claim 1, wherein the skin concern includes one or more of acne, wrinkles, dark spots, and post inflammatory hyper-pigmentation.

3. The computer-implemented method of claim 1, further comprising, recommending, by the computing device, to apply the color-coded substrate in the area of skin affected by the skin concern.

4. The computer-implemented method of claim 1, further comprising, determining, by the computing device, a shape of an area-specific color-coded substrate that conforms to the area of skin.

5. The computer-implemented method of claim 1, further comprising, determining, by the computing device, a color-coded substrate has an active agent that is not compatible with an agent active of another color-coded substrate.

6. The computer-implemented method of claim 1, further comprising, determining, by the computing device, a color-coded substrate is applied to an incorrect area of skin.

7. The computer-implemented method of claim 1, further comprising, determining, by the computing device, a color-coded substrate having an incorrect dosage of active agent is applied to the area of skin.

8. The computer-implemented method of claim 1, further comprising, determining, by the computing device, an elapsed application time of the color-coded substrate exceeds a pre-determined application time, and the computing device sends a notification to remove the color-coded substrate.

9. The computer-implemented method of claim 1, further comprising, determining, by the computing device, a skin concern is increasing or decreasing by comparing a first heat map to a second heat map.

10. A computing device, configured to:
    determine a skin concern and an area of skin affected by the skin concern; and
    determine a color-coded substrate to apply to the area of skin, the color-coded substrate is selected from a plurality of color-coded substrates, wherein each color-coded substrate includes a reinforcing member coated with a composition including at least one hydrocolloid and an active agent, wherein each color-coded substrate has a color, an area-specific shape, and a shape feature, wherein,
    each different color indicates a different active agent,
    each area-specific shape conforms to a specific area of a face or skin, and
    color-coded substrates having a same shape feature indicates compatibility of active agents among color-coded substrates having different colors.

11. The computing device of claim 10, comprising a visible light camera or an infrared camera or both a visible light camera and an infrared camera.

12. The computing device of claim 10, further configured to recommend to apply the color-coded substrate in the area of skin affected by the skin concern.

13. The computing device of claim 10, further configured to determine a shape of an area-specific color-coded substrate that conforms to the area of skin.

14. The computing device of claim 10, further configured to determine a color-coded substrate has an active agent that is not compatible with an agent active of another color-coded substrate.

15. The computing device of claim 10, further configured to determine a color-coded substrate is applied to an incorrect area of skin.

16. The computing device of claim 10, further configured to determine a color-coded substrate having an incorrect dosage of active agent is applied to the area of skin.

17. The computing device of claim 10, further configured to determine an elapsed application time of the color-coded substrate exceeds a pre-determined application time, and the computing device sends a notification to remove the color-coded substrate.

18. The computing device of claim 10, further configured to determine a skin concern is increasing or decreasing by comparing a first heat map to a second heat map.

19. A computer-implemented method of tracking skin concerns, the method comprising:
    determining, by a computing device, a color of a color-coded substrate applied to an area of skin;
    determining, by the computing device, a skin concern associated with the color of the color-coded substrate; and
    determining, by the computing device, an area of skin affected with the skin concern, the color-coded substrate is selected from a plurality of color-coded substrates, wherein each color-coded substrate includes a reinforcing member coated with a composition including at least one hydrocolloid and an active agent, wherein each color-coded substrate has a color, an area-specific shape, and a shape feature, wherein,
    each different color indicates a different active agent,
    each area-specific shape conforms to a specific area of a face or skin, and
    color-coded substrates having a same shape feature indicates compatibility of active agents among color-coded substrates having different colors.

20. A skincare system, comprising:
    circuitry configured to determine a color and geometry of a color-coded substrate responsive to one or more inputs indicative of a presence or absence of a skin concern;
    circuitry configured to tag or classify digital images based on a color and geometry of one or more color-coded substrates applied to the area of skin present in the image;
    circuitry configured to predict a skin concern outcome responsive to a tag or classification indicative of a color and geometry of a color-coded substrate applied to the area of skin, the color-coded substrate is selected from a plurality of color-coded substrates, wherein each color-coded substrate includes a reinforcing member coated with a composition including at least one hydrocolloid and an active agent, wherein each color-coded substrate has a color, an area-specific shape, and a shape feature, wherein,
    each different color indicates a different active agent,
    each area-specific shape conforms to a specific area of a face or skin, and
    color-coded substrates having a same shape feature indicates compatibility of active agents among color-coded substrates having different colors.

21. The skincare system of claim 20, further comprising:
    circuitry configured to generate a digital representation of the area of skin including one or more instances of the predicted skin concern outcome.

22. The skincare system of claim 20, further comprising:
    circuitry configured to generate an alert associated with a time to apply or remove a color-coded substrate, the alert including color and geometry information associated with the color-coded substrate for application or removal.

23. The skincare system of claim 20, wherein the circuitry configured to tag or classify the digital images based on a color and geometry of the one or more color-coded substrates applied to the area of skin present in the image further includes circuitry configured to tag or classify digital images with treatment or active agent information based on a color and geometry of a color-coded substrate applied to the area of skin present in the image.

* * * * *